United States Patent [19]

Tountas

[11] Patent Number: 4,773,419
[45] Date of Patent: Sep. 27, 1988

[54] METHOD AND APPARATUS FOR LIMITING BLOOD FLOW TO A DISTAL PORTION OF AN EXTREMITY

[75] Inventor: Chris P. Tountas, Mendota Heights, Minn.

[73] Assignee: Scanlan International, Inc., St. Paul, Minn.

[21] Appl. No.: 38,422

[22] Filed: Apr. 14, 1987

Related U.S. Application Data

[63] Continuation of Ser. No. 775,496, Sep. 12, 1985, abandoned.

[51] Int. Cl.⁴ .............................................. A61B 17/12
[52] U.S. Cl. .................................. 128/327; 604/207; 128/686
[58] Field of Search ............... 128/326, 327, 344, 346, 128/DIG. 25, 686, 774, 779; 604/97, 228, 133, 135, 242, 143, 152, 905, 207; 403/348, 349

[56] References Cited

U.S. PATENT DOCUMENTS

| | | | |
|---|---|---|---|
| 1,835,122 | 12/1931 | Thévenot | 604/135 |
| 2,309,502 | 1/1943 | Douglas | 604/135 |
| 2,317,729 | 4/1943 | Bruno | 403/348 |
| 2,413,303 | 12/1946 | Folkman | 604/135 |
| 2,533,924 | 12/1950 | Foley | 128/327 |
| 2,617,166 | 11/1952 | Kaufmann | 403/349 |
| 2,660,174 | 11/1953 | Saemann | 128/327 |
| 2,933,087 | 4/1960 | Hamilton | 604/207 |
| 3,083,708 | 4/1963 | Gottfried | 128/39 |
| 3,120,846 | 2/1964 | Fletcher | 128/327 |
| 3,548,819 | 12/1970 | Davis et al. | 128/82.1 |
| 3,563,098 | 2/1971 | Gley | 604/135 |
| 3,633,567 | 1/1972 | Sarnoff | 128/327 |
| 3,745,998 | 7/1973 | Rose | 128/89 R |
| 3,949,748 | 4/1976 | Malmin | 604/135 |
| 4,033,337 | 7/1977 | Raczkowski | 128/2.05 C |
| 4,036,232 | 7/1977 | Genese | 604/143 |
| 4,168,063 | 9/1979 | Rowland | 273/54 B |
| 4,231,494 | 11/1980 | Greenwood | 403/348 |
| 4,331,133 | 5/1982 | Arkans | 128/87 R |
| 4,372,297 | 2/1983 | Perlin | 128/64 |
| 4,378,009 | 3/1983 | Rowley et al. | 128/83 |
| 4,404,862 | 9/1983 | Harris | 604/207 |
| 4,452,546 | 6/1984 | Hiltebrandt | 403/349 |
| 4,494,555 | 1/1985 | Abrioux | 403/348 |
| 4,635,635 | 1/1987 | Robinette-Lehman | 128/327 |

FOREIGN PATENT DOCUMENTS

2326110 5/1977 France .............................. 128/326

OTHER PUBLICATIONS

Letter distributed by Chris P. Tountas (Applicant) in 1980 which discloses a "micropneumatic digital tourniquet".

Primary Examiner—William L. Freeh
Attorney, Agent, or Firm—Merchant, Gould, Smith, Edell, Welter & Schmidt

[57] ABSTRACT

An improved method and apparatus (10) for applying a circumferential pressure to an extremity to control blood flow to a distal portion of the extremity. One embodiment (10) of the apparatus of the present invention includes an inflation device (12), an inflatable cuff (14) and a tube (16) interconnecting the inflation device (12) and the inflatable cuff (14). The inflation device (12) preferably includes a syringe pump (18) and a spring unit (20). The spring unit (20) includes a compression spring (36) which resiliently applies a force to the plunger (24) of the syringe pump (18), thereby applying a continuous pressure to the fluid within the syringe cylinder (22). The cuff (14) is thereby supplied with a controlled pressure to control the blood flow through the encircled portion of the extremity.

9 Claims, 2 Drawing Sheets

METHOD AND APPARATUS FOR LIMITING BLOOD FLOW TO A DISTAL PORTION OF AN EXTREMITY

This is a continuation of application Ser. No. 775,496, filed Sept. 12, 1985, now abandoned.

FIELD OF THE INVENTION

The present invention relates generally to tourniquets. More specifically, it relates to tourniquets that are pressurized by a fluid (e.g., air) to produce a degree of circumferential pressure about an extremity that is both effective and safe.

BACKGROUND OF THE INVENTION

Tourniquets are well-known devices for applying pressure to an appendage or extremity to limit the flow of arterial blood therethrough. They have been used as a "first aid" treatment of hemorrhaging limbs and also as means for creating ischemia in a surgical field. Although the present invention could be used as a "first aid" method and apparatus, the following discussion will focus primarily on surgical applications for the sake of brevity.

Tourniquets are used during surgery of the extremities so that procedures may be performed in a bloodless surgical field. Typically, a tourniquet is applied to a proximal portion of an extremity to limit blood flow to a distal portion of an extremity. For example, a tourniquet is often wrapped about the proximal portion of a finger which is to be operated on near its distal tip.

An early technique involved wrapping a rubber bandage, known as an Esmarch bandage, tightly around an extremity to exsanguinate the blood and to cut off the circulation. The pressure created by an Esmarch bandage can be very great, and this method has largely been abandoned in favor of carefully monitored pneumatic tourniquets since the excessive pressure associated with the improper use of an Esmarch bandage has been known to damage delicate neuronal tissue, resulting in neuropraxia and pain. The present invention is directed to such pneumatic tourniquets, and more generally to fluid-operated tourniquets, wherein pressurized fluid causes a cuff to circumferentially compress an extremity. The cuff fluid can be any liquid or gas or combination thereof, but the present discussion will be directed primarily to pneumatic embodiments.

While a number of pneumatic cuffs and inflation systems are available for use on arms and legs, application of these devices on the distal parts of extremities, i.e. wrists, ankles, fingers, and toes, is generally not feasible. Moreover, some current surgical tourniquet systems lack ease of portability and thus are found in operating rooms but are not available in emergency rooms and clinics. As a result, surgery on an isolated finger, for example, is usually accomplished with application of an Esmarch bandage type of tourniquet, often a makeshift piece of rubber capable of creating excessive pressure and irreversible damage to nerves and vessels.

In addition, prior art pneumatic tourniquet systems generally fail to include a mechanism for compensating for increases or decreases in cuff air pressure. A decrease in the air pressure can be caused by a slow leak, for example.

The present invention is directed to the problems addressed above. In particular, the present invention includes an apparatus for limiting blood flow through an extremity which includes means for safely limiting the fluid pressure within the cuff. In addition, the pressure limiting means preferably serves to substantially maintain the preset pressure within the cuff in the event of a slow leak, for example. Finally, preferred embodiments of the apparatus of the present invention are portable and inexpensive, making them practical for operating room, emergency room and clinical use.

SUMMARY OF THE INVENTION

Accordingly, in broad terms the apparatus of the present invention includes means for containing a fluid having an internal volume; means for placing the fluid containing means in fluid communication with a tourniquet cuff; means operatively connected to the fluid containing means for reducing its internal volume; and resilient means operatively connected to the internal volume connecting means. In operation, distortion of the resilient means generates a force on the internal volume reducing means which pressurizes a fluid within the fluid containing means which in turn urges the cuff toward the extremity to apply a circumferential pressure thereto.

The apparatus of the present invention also includes an entire fluid-operated tourniquet which includes a cuff means for substantially encircling the extremity.

Preferred embodiments of the apparatus of the present invention include a substantially tubular bladder made of latex rubber. The bladder is in fluid communication with the fluid containing means, whereby when the internal volume of the fluid containing means is reduced the bladder is inflated (when the fluid is air) and the bladder is urged toward the extremity to apply a circumferential pressure thereto.

Preferred embodiments also include a syringe cylinder as the fluid containing means and a syringe plunger as the means for reducing the internal volume of the fluid containing means. Further, preferred embodiments include a compression spring in operative contact with the syringe plunger whereby when it is desired to pressurize the cuff the spring is distorted so as to exert a continuous force on the syringe plunger, thereby putting the fluid within the syringe cylinder under pressure.

Preferably, the "resilient means" further includes a spring housing which is removably attachable to the syringe cylinder, wherein the spring housing contains the compression spring which acts on the syringe plunger. In preferred embodiments, the spring housing includes a female bayonet member and the syringe cylinder includes a male bayonet member, e.g., projections adjacent the circular plunger opening in the cylinder.

In addition, preferred embodiments include hook and loop portions which are attachable to cause the inflatable bladder to snuggly encircle the extremity.

The invention also includes a method for supplying a fluid to a tourniquet cuff. The method includes selecting a container suitable for containing the fluid; placing the fluid container in fluid communication with the cuff; positioning means in contact with the container for reducing its internal volume; placing a resilient element in operative contact with the internal volume reducing means; and distorting the resilient element to apply a force to the internal volume reducing means. The distortion of the resilient element causes a force to be applied to the internal volume reducing means which pressurizes the fluid supplying the cuff.

Another method of the present invention includes selecting a cuff and placing it in fluid communication with the fluid container.

DETAILED DESCRIPTION OF THE INVENTION

Figure 1:
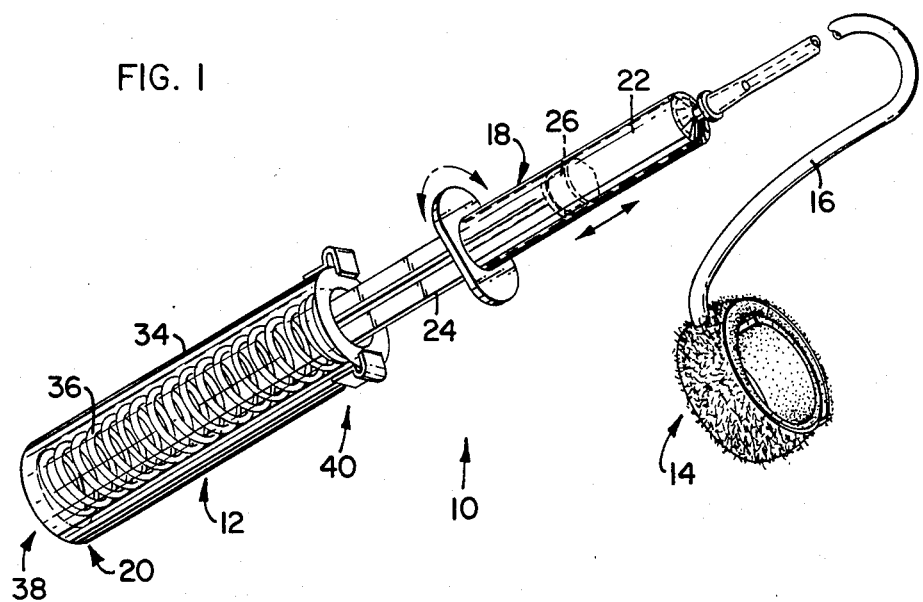
FIG. 1 is a perspective view of one embodiment of the present invention, illustrating a digital cuff and an inflation device.

A preferred embodiment of the invention will be described in detail with reference to the drawing, wherein like reference numerals represent like parts and assemblies throughout the several views. Reference to this preferred embodiment does not limit the scope of the invention which is limited only by the scope of the claims interpreted according to the Doctrine of Equivalents.

Referring now to the attached drawing, FIG. 1 perspectively illustrates a preferred tourniquet 10 of the present invention. The tourniquet 10 is preferably a separable combination of an inflation device 12 and a cuff 14. A flexible tube 16 connects the inflation device 12 to the cuff 14 and places the two components in fluid communication so that when the inflation device 12 is activated it supplies pressurized air to the cuff 14. Preferably, the tube 16 is latex rubber tubing which can be detached from the inflation device 12. The inflation device 12 and cuff 14 are further described below.

As shown in FIG. 1, the inflation device 12 preferably includes a standard syringe pump 18 and a spring unit 20. As described further below, the pump 18 and the spring unit 20 are interconnected to activate the inflation device 12 and are disconnected to remove and reset the tourniquet 10.

As noted above, the inflation device 12 preferably includes a standard syringe pump 18. Such syringe pumps are well-known to those skilled in the art and include a syringe cylinder 22 and an axially aligned syringe plunger 24. At one end of the plunger 24 is a rubber piston 26 which forms an air-tight fit in the syringe cylinder 22. At the other end of the plunger 24 is a plunger button 28, shown in FIGS. 2 and 3.

The syringe cylinder 22 narrows down to form a syringe tip 30 at one end. The tip 30 is suitable for receiving the flexible tubing 16 which connects the cylinder 22 to the cuff 14. The opposite end of the syringe cylinder 22 forms two diametrally spaced ear-like projections 32 which outwardly extend in perpendicular fashion from the cylinder 22.

As noted above, the inflation device 12 also includes a spring unit 20. The spring unit 20, shown in cross section in FIGS. 2 and 3, includes a tubular housing 34 which contains an axially-aligned compression spring 36. The housing 34 has a closed distal end 38 and an open proximal end 40, wherein the opening is indicated with the reference numeral 44. One end of the spring 36 abuts the closed end 38 of housing 34. The opposite end of the extension spring 36 is in operative proximity of the opening 44. Further, the spring 36 is preferably axially aligned with the plunger 24 and the syringe cylinder 22.

Figure 3:
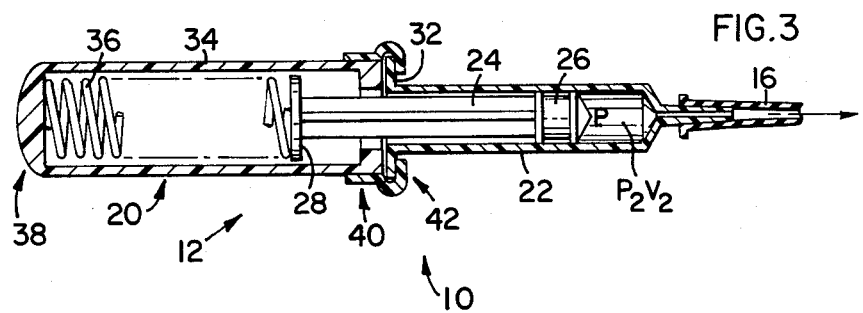
FIG. 3 shows a longitudinal cross-sectional view of the embodiment of FIG. 1, wherein the inflation device is activated.
Figure 6:
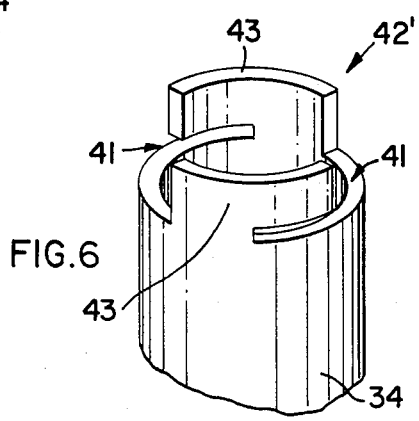
FIG. 6 shows an enlarged perspective view of a female bayonet fitting on an alternative embodiment of a spring housing.

Fixed on the outside of housing 34 adjacent to its proximal end 40 is a female receiving member 42 which is suitable for receiving the projections 32 extending radially outward from the syringe cylinder 22. FIG. 6 shows an alternative locking member, a female bayonet member 42'. The member 42 or 42' includes a pair of diametrally spaced slots 41 formed by tabs 43 suitable for receiving and holding the projections 32 on the cylinder 22. Once the projections 32 have been aligned with the corresponding curved slots 41 in the member 42 or 42' the syringe cylinder is rotated relative to the housing 34 in a well-known manner to lock the two components together. FIG. 3 illustrates this locked state wherein the projections 32 are held by the female locking member 42 or 42' to lock the spring unit 20 to the pump 18.

The housing 34 can be made using any conventional material and fabrication techniques. Preferably, however, the housing 34 is made of injection molded plastic, e.g., polyethylene. The housing 34 can be transparent or opaque. If the housing 34 is transparent, the degree of compression of the spring 36 can be directly observed and this can be translated into the amount of air pressure in the cylinder 22 and in the cuff 14.

The spring 36 is preferably a conventional compression spring. For a preferred digital tourniquet embodiment, the compression spring has a rate or modulus of 2.5 pounds per inch. Of course, this spring rate will vary depending on the area of piston 26, but for a standard 5 cc syringe having a nominal inside diameter of ½ inch, the spring rate is preferably 2.5 pounds per inch. If the area of the piston 26 is larger than that for a standard 5 cc syringe, then the spring rate should be higher; on the other hand, if the piston area is smaller, the spring rate should be smaller. In any case, the spring rate and the piston diameter should be chosen to generate a pressure in the cylinder 22 and the cuff 14 which never exceeds the safe operating pressure. For a digital tourniquet, it is generally recommended that the maximum pressure not exceed 450 mm Hg. Those skilled in the art will recognize that the pressure developed in the cylinder 22 depends not only on the spring rate and piston area but also on the initial position of the piston 26. If the piston 26 is initially positioned near the opening of the cylinder 22 which accepts the plunger 24, the pressure which can be generated in the cuff 14 is larger. On the other hand, if the piston 26 is initially positioned closer to the tip of the cylinder 22 the amount of pressure generated in the cylinder 22 when the housing 34 is connected to the cylinder 22 will be smaller.

As noted above, the housing 34 forms an opening 44 in its proximal end 40 suitable for receiving the syringe plunger 24. The opening 44 is smaller than the plunger button 28 and therefore the syringe plunger 24 cannot be completely withdrawn from the housing 34 or pushed out of the housing 34 by the spring 36.

Figure 4:
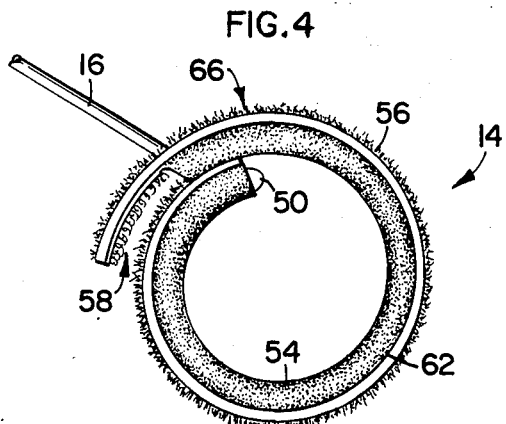
FIG. 4 shows an enlarged side elevational view of the cuff of the embodiment of FIG. 1.
Figure 5:
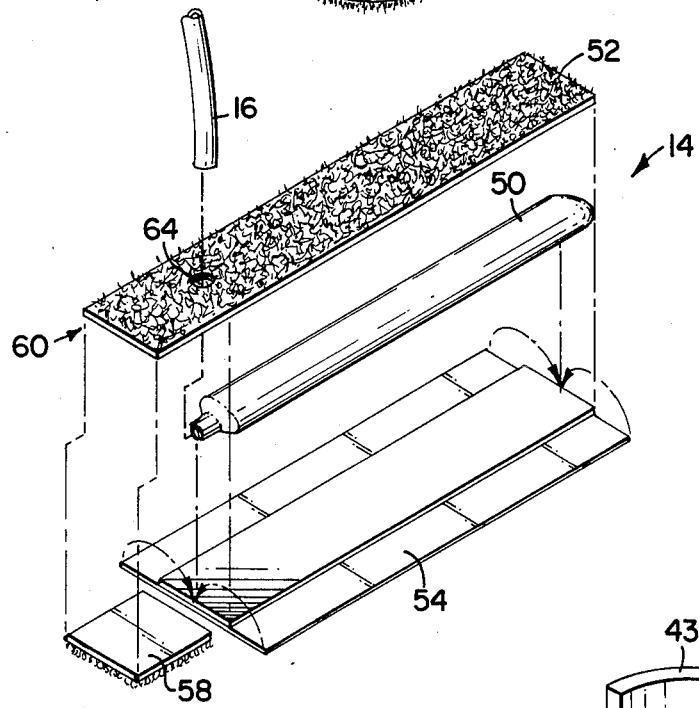
FIG. 5 shows an enlarged exploded view of the cuff of the embodiment of FIG. 1.

Enlarged views of the tourniquet cuff 14 are shown in FIGS. 4 and 5. FIG. 5 is an exploded view of the cuff 14. The cuff 14 preferably includes a tubular rubber bladder 50 which is in fluid communication with the tube 16 running to the inflation device 12. The rubber bladder 50 is preferably made of latex rubber according to standard dipping fabrication techniques.

The rubber bladder 50 is preferably sandwiched between a strip of non-extensible fabric 52 on the exterior surface of the cuff 14 and a strip of extensible fabric 54 on the inner surface of the cuff 14. The non-extensible fabric 52 is preferably a woven material which is covered on its outer surface 56 with a strip of the "loop" portion of "hook and loop" or Velcro ™ material. The rubber bladder 50 has an opening at one end which is connected to the tube 16. Access to the bladder 50 is provided through a hole 64 formed in the non-extensible fabric 52. In addition, a piece of "hook" material 58 is attached to the underside of one end 60 of the non-extensible fabric 52.

The extensible fabric 54 is nylon tricot, for example, which is attached to the underside of the nonextensible fabric 52 by means of adhesive or stitching on the edges of the strips 52 and 54. Thus, the bladder 50 is sandwiched between the fabrics 52 and 54 without being directly attached to them. The fabric strips 52 and 54 form an elongated pouch suitable for holding the bladder 50.

FIG. 4 shows an elevational view of the cuff 14 in its assembled state. The fully assembled cuff 14 is depicted in the coiled state it would assume when it was being used. A seam 62 between the extensible and non-extensible fabrics 54 and 52, respectively, is illustrated. The hook material 58 on the end 60 of the non-extensible fabric 52 is shown in position ready for attachment to the loop surface 56 on the non-extensible fabric 52 to complete the encirclement of the cuff 14 about the extremity. The bladder 50 is barely visible in FIG. 4, protruding slightly from the end of the pouch formed by fabric strips 52 and 54 proximate the end of non-extensible fabric 52 opposite from end 60. The bladder 50 is connected to inflation tube 16 which exits from the hole 64 in the non-extensible fabric 52.

Referring to FIG. 4, it should be noted that the coiled bladder 50, which extends from the hole 64 in the non-extensible fabric 52 to the distal tips of the fabric strips 52 and 54, overlaps at 66. Overlap helps to provide uniform pressure over the entire periphery of the extremity. This is normally accomplished in prior art cuffs by placing the inflation tube in the middle of the bladder and overlapping the two ends. The bladder 50 of the present invention, on the other hand, is unique in that the thin wall and high elongation of dipped latex rubber permit easy inflation from one end of the bladder in spite of the constriction form at 66. The low resistance to stretching is an advantage for patient comfort as well, since it gives greater conformability and more uniform transmission of pressure from the bladder to the underlying tissue. The extensible fabric 54 covering the bladder 50 assists in performance of the cuff 14 by controlling lateral expansion of the bladder 50.

Operation of the tourniquet 10 can now be described. The following description will assume that the tourniquet 10 is for digits but it should be stressed that the present invention can be used on other extremities, including ankles and wrists.

The cuff 14 is first snuggly wrapped about a patient's digit by encircling it with the cuff 14 in the manner shown in FIG. 4. Once the cuff 14 is snuggly wrapped about the patient's digit, the hook material 58 is pressed into engagement with the loop material 56 on fabric 52. The cuff 14 is preferably sized so as to overlap at point 66 shown in FIG. 4. As noted above, an overlap provides a more uniform pressure about the entire extremity.

With the cuff 14 snuggly wrapped on the patient's digit the tube 16 is connected to the tip 30 of syringe cylinder 22. The piston 26 of syringe plunger 24 is then inserted into cylinder 22 and pressure is applied to the distal end 38 of housing 34 so as to compress spring 36. The spring 36 bears on plunger button 28 which causes the piston 26 to compress the air within the syringe cylinder 22. The pressurized air is communicated to the cuff 14 by the tube 16 and the bladder 50 is thereby inflated creating a peripheral or circumferential pressure about the patient's digit.

The housing 34 is further depressed until the projections 32 can be inserted into and locked with lock member 42 or 42' on the proximal end 40 of housing 34. Once the housing 34 and cylinder 22 are locked together, the spring 36 continues to act on plunger 24 to compress the air within the cylinder 22, tube 16 and cuff 14. Thus the spring acts to maintain the pressure within the cuff 14. In the event of a slow leak or other disturbance which would otherwise cause an unacceptable decrease in the pressure within the cuff 14, the spring 36 extends to maintain a pressure within the cuff 14. Likewise, if the pressure within the cuff 14 increases due to an increase in the temperature of the air, for example, the spring 36 compresses to increase the volume within the syringe cylinder 22 to relieve the otherwise excessive pressure.

Figure 2:
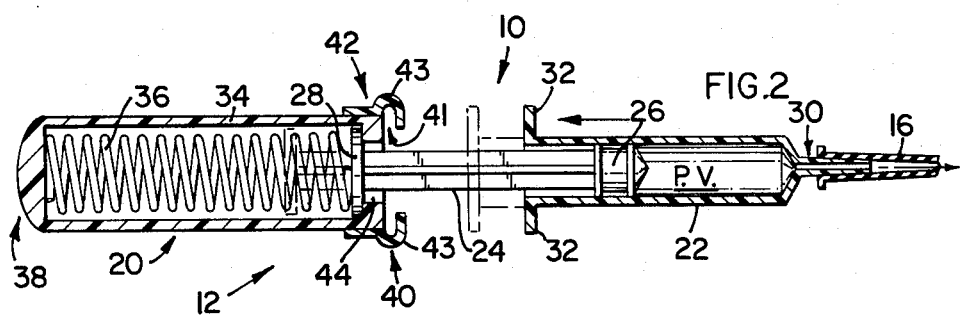
FIG. 2 is a longitudinal cross-sectional view of the inflation device of the embodiment shown in the FIG. 1, wherein the inflation device is not activated.

The effect of engaging the housing 34 and the cylinder 22 can be readily seen in FIGS. 2 and 3. The act of engaging the cylinder 22 with the spring housing 34 causes the spring 36 to compress and exert a force on the plunger 24 which in turn moves the piston 26 down the cylinder 22 to a new position. The initial pressure in the cylinder 22, $P_1$ (generally atmospheric pressure), is thereby increased to a higher value, $P_2$, in proportion to the decrease in volume from $V_1$ to $V_2$ since the produce of pressure and volume is constant at a constant temperature according to well-known principles. The pressure within the cuff 14 is determined primarily by the force exerted by the spring 36 on the piston 26 and the diameter of piston 26. Thus, the inflation device 12 of the present invention substantially ensures that excessive pressure will not develop in the cuff 14 since the piston diameter and maximum spring force will be appropriately specified and controlled during the manufacture of devices 10.

It should be noted that a submaximal pressure can be achieved by selecting an initial position for the piston 26, with the cuff 14 detached, which is farther down the cylinder 22 toward the tip 30 of the cylinder 22. This is due to the fact that the spring 26 will exert less force on the plunger 24 when the spring 36 is compressed to a lesser degree prior to locking the cylinder 22 to the housing 24. Thus an advantage of the present invention is that the cuff pressure can be calibrated with respect to the final position of the plunger piston.

One way to calibrate the inflation device 12 is to mark a "green zone" or "safe zone" on the transparent cylinder 22. Assuming that the initial position of the piston 26 is always at the mouth of the cylinder 22 opposite the tip 30, then engaging the cylinder 22 with the spring housing 34 will develop maximal pressure and the position of the piston 26 will be "above" the safe or green zone. By partially detaching the tube 16 from the syringe tip 30 to bleed off some pressurized air, the plunger piston 26 can be slowly moved into the safe or green zone which will ensure that the pressure within cuff 14 is not too low or too high. If, during operation, the piston 26 moves "below" the green zone due to a leak, for example, the piston 26 should be withdrawn from cylinder 22 and the housing 34 and cylinder 22 should be reengaged following correction of the problem.

As noted above, the present invention can be used with any extremity, including a digit. If the tourniquet device 10 is being used for digits, the pressure within the cuff 14 should preferably be between approximately 200 and 350 millimeters of mercury. Of course, this depends on the patient's maximum blood pressure since the pressure within the cuff must exceed the patient's blood pressure in order to create ischemic conditions.

If the tourniquet 10 is to be used for ankles or wrists, the entire tourniquet 10 can simply be upsized from the digital tourniquet described above. The cuff 14 would preferably be of similar construction but would merely be larger and the inflation device 12 would also be proportionately larger. For example, the digital tourniquet can use a 5 cc syringe whereas the ankle or wrist tourniquet might use a 50 cc syringe.

It should be emphasized that the present invention is not limited to any particular materials or combination of materials, and modifications of the invention will be apparent to those skilled in the art in light of the foregoing description. This description is intended to provide specific examples of individual embodiments which clearly disclose the present invention. Accordingly, the invention is not limited to these embodiments or to the use of elements having the specific configurations and shapes as presented herein. All alternative modifications and variations of the present invention which fall within the spirit and broad scope of the appended claims are included.

I claim:

1. A pneumatic tourniquet for substantially encircling an extremity and distributing pressure developed by a fluid contained by said tourniquet to the extremity to control blood flow to a distal portion of the extremity, comprising:
   (a) a cuff suitable for encircling the extremity;
   (b) a transparent cylinder for containing the fluid having an internal volume and having means for calibration of tourniquet pressure on said cylinder;
   (c) means for placing the cylinder in fluid communication with the cuff;
   (d) a plunger suitable for slidable sealing contact with the cylinder for reducing its internal volume;
   (e) a spring housing suitable for operatively connecting to the cylinder; and
   (f) a compression spring suitable for bearing on the spring housing and the plunger, wherein when the apparatus is supplied with the fluid, and when the spring housing is operatively connected to the cylinder in a single manual compressive stroke, the compression spring applies a force on the plunger which pressurizes the fluid within the cylinder which in turn urges the cuff towards the extremity to apply the pressure thereto less than or equal to 450 mmHg said spring maintaining pressure of the fluid in the cuff and wherein establishment of pressure in the range of 200 to 300 mmHg can readily be confirmed by visual inspection of the position of the plunger within the cylinder by its alignment with said calibration means on said cylinder, whereby blood flow to the distal portion of the extremity is controlled.

2. The apparatus of claim 1, wherein said calibration means comprises marking a zone on said transparent cylinder.

3. The apparatus of claim 1, wherein the fluid is air.

4. The apparatus of claim 3, wherein the cuff means comprises an inflatable bladder, and wherein the cylinder is a syringe cylinder and the plunger is a syringe plunger.

5. The apparatus of claim 4, wherein the cuff means comprises a layer of substantially nonextensible material and a layer of extensible material, wherein the layers of material are attached to form a pouch suitable for receiving the inflatable bladder.

6. The apparatus of claim 4, wherein the cuff means comprises a hook portion and a loop portion, wherein the hook and loop portions are selectively attachable to substantially encircle the bladder about the extremity.

7. The apparatus of claim 6, wherein the bladder is substantially tubular, has two ends, and is made of latex rubber, wherein the bladder comprises an inlet at one of its ends in fluid communication with the syringe cylinder.

8. The apparatus of claim 4, wherein the spring housing is removably attachable to the syringe cylinder, wherein when the spring housing is attached to the syringe cylinder the compression spring resiliently engages the syringe plunger to compress the fluid.

9. The apparatus of claim 8, wherein the spring housing comprises a female bayonet member and the syringe cylinder comprises a male bayonet member, wherein the bayonet members are selectively attachable.

* * * * *